United States Patent
Sharon et al.

(10) Patent No.: US 7,402,433 B2
(45) Date of Patent: Jul. 22, 2008

(54) **METHOD OF IN-VITRO MICROPROPAGATION OF *PIPER LONGUM* PLANTS**

(75) Inventors: Madhuri Sharon, Mumbai (IN); Ghanshyam Maurya, Jamnagar (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 792 days.

(21) Appl. No.: 10/411,151

(22) Filed: Apr. 10, 2003

(65) Prior Publication Data
US 2004/0203151 A1 Oct. 14, 2004

(51) Int. Cl.
*A01H 1/00* (2006.01)
*A01H 1/02* (2006.01)
*C12N 5/00* (2006.01)
*C12N 5/02* (2006.01)

(52) U.S. Cl. ............... 435/430; 435/430.1; 435/431; 435/420; 800/298; 800/295; 47/58.1 R

(58) Field of Classification Search ............ 800/298; 435/430, 430.1
See application file for complete search history.

(56) References Cited

OTHER PUBLICATIONS

Sarasan et al. Journal of Spices and Aromatic Crops 2 (1 &2): 34-40 (1993).*
Bhatt et al. Plant Cell reports (1995) 14:398-402.*
Soniya et al. Plant Cell, Tissue and Organ Culture (2002) 70:325-327.*
Marie De Fatima et al (In Vitro Cell Dev. Biol-Plant (1996)32:199-203).*

* cited by examiner

*Primary Examiner*—Medina A Ibrahim
(74) *Attorney, Agent, or Firm*—J. Harold Nissen; Lackenbach Siegel, LLP

(57) ABSTRACT

The present invention relates to an efficient method of in-vitro micropropagation of *Piper longum* plants. In particular, the present invention is directed towards the novel method for micropropagation of *Piper longum* from lateral bud (meristematic) explant (starting material), by culturing the explants on different medias. This method results in mass production of the plant *Piper longum* in a short span of time.

7 Claims, 7 Drawing Sheets

METHOD OF IN-VITRO MICROPROPAGATION OF *PIPER LONGUM* PLANTS

FIELD OF THE INVENTION

This invention relates to an efficient method of in-vitro micropropagation of *Piper longum* plants. In particular, the present invention is directed towards the novel method for micropropagation of *Piper longum* from a lateral bud explant (starting material), by culturing the explants on different media.

BACKGROUND OF THE INFORMATION

Plants have been used for medicinal application ever since man began caring for his body and health. For centuries, the world has depended on the valuable properties of plant as a source of healing. Ayurveda, Siddha, Unani and Homeopathy continue to depend predominantly on medicinal and aromatic plants as raw material for the formulation of drugs.

Medicinal Plants have attracted attention of not only professionals from various systems of Medicine, but also the scientific community belonging to different disciplines. From time immemorial, medicinal plants are known and are being used since then. Based on the considerable knowledge about these plant species from the ancient books, the modern system of medicine have enabled these plants find a place in the commercial market.

Medicinal plants are growing in importance day by day, because of the widespread interest in the adoption of multiple approaches to health care. Medicinal plants and products derived from them, have a unique place in both preventive as well as curative medicine, as these plants produce an immense and diverse array of organic compounds, called secondary metabolites. Considerable efforts are being made all over the world, to utilize more and more plant resources, as the medicine of today is found to shift from synthetic molecules to naturally synthesized molecules. Also, these naturally synthesized molecules are biologically more compatible and less toxic to human system as compared to synthetics. The majority of natural products used medicinally in plants are secondary metabolites viz., terpenoids, steroids, cardenolides, quinine lignans, flavonoids or alkaloids. Medicinal plants have gained pharmaceutical importance/therapeutic value due to its specific constituents/combination of secondary metabolites present in them. These metabolites are often differentially distributed among limited taxonomic groups within the plant kingdom and participate in interesting biological activities that can have high therapeutic value.

One such medicinal plant species that has gained pharmaceutical importance is *Piper longum* commonly known as long pepper. *Piper longum*, is a slender aromatic, perennial climber belonging to the family Piperaceae, with thin and erect branches having sessile ovate leaves. It has minute dioecious flowers on spikes (inflorescence). Fruits, which are used in medicine, are small red berries and often turns black on ripening. It grows well in tropical and subtropical climate.

The compound of medicinal interest in *Piper longum* is present in the female spike (inflorescence). *Piper longum* plant contains alkaloid piperine as one of the active ingredient. Other active ingredients present in *Piper longum* plant are various amides viz. futoamide (Das & Kashinatham 1998), alkamide (Das & Kashinatham 1996), a new dimmer of amide (Zang & Wang 1996), some minor amides (Kaul & Taneja 1998) and an amide alkaloid (piperlongumine).

The dry female spike of *Piper longum* is widely used in Ayurvedic and Unani system of medicine particularly for diseases of respiratory tract. It is a powerful stimulant of both digestive and respiratory system and has been shown to have rejuvenating effect on lungs. It is known to play an important role in aiding the thermogenic response i.e. the result of increased thyroid hormone level in the body makes *Piper longum* a typical Ayurvedic complementary component whose benefit is to increase the bio-availability and to enhance the uptake of the other active ingredients. It is accepted as immuno-potentiating agent (Dahanukar 1991) and has shown promises as hepato-protective medicinal plant during clinical trials (Doshi et al 1994). The root of this plant is used for stomachache and is also prescribed in palsy, gout, rheumatism and lumbago.

Cultivation of *Piper longum* till recently was not very common. However, with increasing market demand of *Piper longum*, efforts are being diverted towards systematic cultivation of *Piper longum*. Since *Piper longum* is a shade loving creeper, majority of cultivators grow them as intercrop in coffee, arecanut & coconut plantation. Laterite soil, soil rich in organic matter are suitable for cultivation of *Piper longum*.

Conventionally, *Piper longum* is cultivated through planting matierals such as suckers, stem cuttings, seeds or rooted vine cuttings in the month between March-April and later on transplanted in June at the onset of monsoon.

The following are the drawbacks associated with conventional method of cultivation of *Piper longum* using seed, suckers, rooted stem cuttings respectively.

Seeds as planting material: Very rarely seeds are used as planting material, because number of viable seeds produced by one spike is very limited. Since, female spikes are the medicinal part of the plant, available seeds material for plantation is very less or limited. Moreover, *Piper longum* seeds are highly heterozygous in nature hence do not ensure quality homogenous raw material production. As seeds produce heterozygous plant (offspring), hence are not a good choice material.

Suckers as planting material: Suckers are produced only from adult plants. They are produced after two years of plantation. Moreover, a plant produces very limited number of suckers, thus very small number of planting material is available. This method is commercially not very viable as, *Piper longum* has woody roots which develops in 2-3 years old plant. From woody roots, few suckers develop which can be used for plantation. However, this method does not provide enough planting material.

Rooted stem cuttings as planting material: The most common cultivation practice is from rooted stem cuttings. 8-10 cm long stem segments are taken from the tip of the branches & artificially rooted using rooting hormone. Only 70-80% cuttings develop rootings. These are then transplanted in monsoon to the field with as much as 95% survival. The only snag with this method is that, when from a mature plant more than 4-5 stem cuttings are taken, these plants show reduced yield and growth. It is noticed that if more than 10% plants are used from a commercial cultivation field for generating the cuttings, it severely affects the production of raw material.

The existing methods of cultivating *Piper longum*, is time consuming, as time is lost in preparing stem cuttings, rooted vines or suckers for plantation of *Piper longum*. All this reduces the plant population which plant otherwise have given female spike or roots having medicinal properties.

Contrary to this, the rate of multiplication by micropropagation is much higher and in a shorter time. Moreover, by micropropagation one can develop clones as well as somaclonal variants for selection of desired traits.

Plant regeneration by tissue culture techniques is well established. A wide variety of plant species has been successfully micropropagated in vitro via organogenesis or somatic embryogenesis. Organogenesis leads to organ formation i.e. shoot or root, which can be isolated to induce development of roots or shoots, to produce full plant. While somatic embryogenesis leads to the development of somatic embryos (embryos developed without fertilization) which have both shoot and root initials and are capable of developing into whole plant. Although the ability of individual parts of plants and cells to regenerate into complete plants called totipotency, is a well known phenomenon, each plant or plant part requires specialized studies to invent the conditions that allow such regeneration. Some of the broadly applicable factors controlling growth and differentiation of such cultures have been determined. The establishment of interactions among different groups of phytohormones and growth regulators alone or in combinations are responsible for certain interrelations existing among cells, tissues and organs. There seems to be consensus that the success in inducing differentiation depends upon the type of explant, physiological condition of the explant and physical and chemical milieu of the explant during culture. Due to this, the science of tissue culture has been directed to optimize the physiological conditions of source plant, the type of explant, the culture conditions and the phytohormones used to initiate tissue culture. This substantiates the fact that development of a new process for proliferation of plants by tissue culture is not obvious.

There is no report on micropropagation of *Piper longum* from lateral bud explant through direct rhizogenesis (organogenesis) followed by the plant regeneration. The scientist of the present invention have been successful in developing an efficient in vitro system of micropropagation of *Piper longum* from lateral bud explant through direct organogenesis.

There is an urgent need to develop a method which obviates the drawbacks of the existing protocols. Looking at above mentioned problems related to availability of planting material, it is imperative that the novel method of producing elite, homogenous planting material is developed. Keeping this in mind the present work has been undertaken. The present invention provides an efficient and cost effective method of in-vitro micropropagation of *Piper longum*. By this method the raw material of *Piper longum* produced is as high as 900 times the conventional methods, in less number of days.

OBJECTS OF THE INVENTION

It is an object of the present invention, to develop a highly efficient, commercially viable micropropagation system of *Piper longum*, by in vitro culture or tissue culture.

It is an object of the present invention to select the explant, lateral bud (meristematic), and their isolation parameters from healthy growing plants, under controlled condition.

It is yet another object of the present invention to develop a sterilization system for surface sterilization of explants without damaging the isolated tissues.

It is yet another object of the present invention to develop a nutrient media requirement including growth regulators for (a) culture initiation from the explant (b) shoot bud proliferation on initiated cultures and shoot elongation (c) rooting of regenerated shoots.

It is yet another object of the present invention to standardize the physical parameters viz. photoperiod, light intensity, relative humidity and temperature for all the stages of in vitro culture.

It is yet another object of the present invention to find out the time interval at which a subculture of different culture stages could be performed.

It is yet another object of the present invention to harden the in vitro cultured plants so that they can be acclimatized and safely transferred from lab to land.

SUMMARY OF THE INVENTION

The present invention relates to an efficient method of in-vitro micropropagation of *Piper longum* plants. In particular, the present invention is directed towards the novel method for micropropagation of *Piper longum* from lateral bud (meristematic) explant (starting material), by culturing the explants on different medias. This method results in mass production of the plant *Piper longum* in a short span of time.

The present invention involves in-vitro micropropagation of *Piper longum* through direct rhizogenesis (organogenesis) by culturing lateral bud (meristematic) explant on various medias. Conventionally, in vitro induction of rhizogenesis (organogenesis) is achieved from callus derived explants. Whereas, in the present invention, rhizogenesis is achieved directly from meristematic explant. The cells in lateral buds are meristematic i.e. these cells do not have alteration in their DNA sequencing hence a clonal offspring can be produced from them.

In accordance to the present invention, the meristematic cells of the lateral bud explant are transformed into root like appendages, by culturing in dark, on a culture initiation medium consisting of MS basal medium, supplemented with a growth hormone, synthetic auxin NAA. The growth hormone NAA is used for inducing rhizogenesis (root like structure). These root like structures are subsequently grown in light and once it reaches 1.5 cm in length, are cut into 0.5 cm long pieces. These long pieces are inoculated on growth hormone, cytokinin BAP containing nutrient medium. This growth hormone is used as shoot bud inducing medium. The shoots regenerated from the shoot buds are elongated in shoot elongation medium supplemented with natural auxin, thereby promoting shoot elongation. The elongated shoots are then transplanted to MS medium containing IBA for rooting of the shoots, thereby regenerating plantlets of *Piper longum*. These regenerated plantlets are hardened and transferred to the field for cultivation in a conventional manner.

The plant hormone used are auxin and cytokinin of different concentrations.

The auxins are selected from 3-indole butyric acid (IBA), naphthalene acetic acid (NAA), 2,4-Dichlorobenzoic acid (2,4-D), Indole Acetic Acid (IAA), Naphthoxy Acetid Acid (NOA) and the like. The most preferable auxin used in the present invention is NAA, IBA.

The cytokinins are selected from Kinetin, benzyl aminopurine (BAP), 2-iso-Pentenyl adenine (2-iP) and the like. The most preferable cytokinin used in the present invention is BAP.

The culture mediums for micropropagation of the plant *Piper longum* are selected from MS basal medium (Murashige, T & Skoog. F (1962), a B5 medium (Gramborg, O. L. et. al (1968)) and the like. The most preferable culture medium used in the present invention is MS basal medium (Murashige, T. & Skoog (1962).

This invention has several advantages over the conventional protocols. The novel features of the invention are the following:

The method is simple and has a very high frequency of plant multiplication in a short span of time and space.

The lateral bud explant selected from mature *Piper longum* plants are found to respond efficiently, as high as 900 times the conventional methods.

The meristamatic cells by direct rhizogenesis produces clones.

The plants can be produced during all the seasons depending on the requirement.

Nutrient media and growth regulator requirement for each stage of micropropagation (i.e. conversion of an explant into many plantlets) was identified and selected viz. culture initiation, rhizogenesis, induction of adventitious shoot buds, shoot elongation and rooting.

Acclimatization and hardening of regenerated plants reduced the mortality to 0% during transfer of plants to the field.

Figure 1:
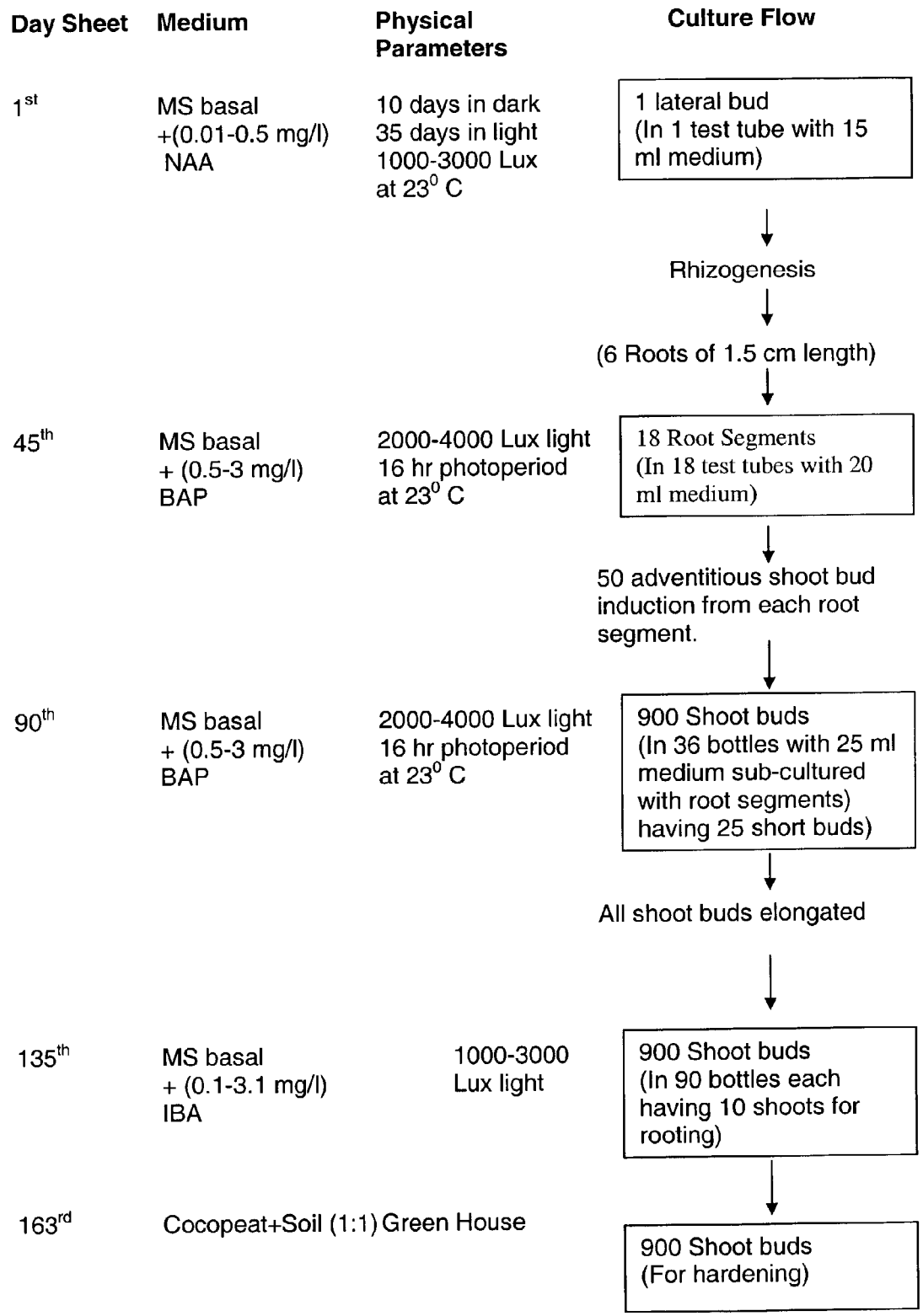
FIG. 1 shows a flow diagram for the micropropagation of *Piper longum* via direct rhizogenesis (organogenesis) derived from non sexual meristematic explant tissues.
Figure 2:
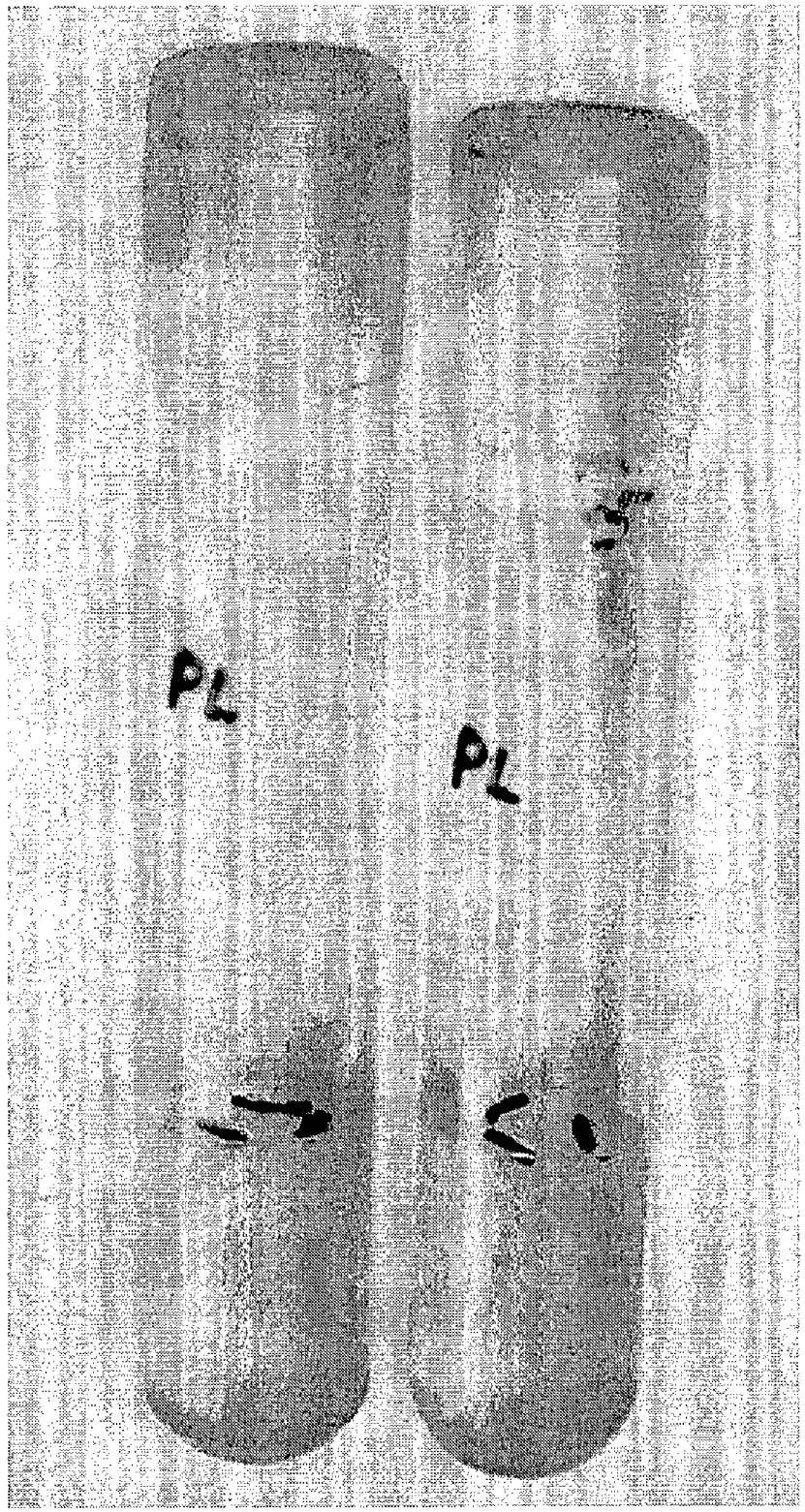
FIG. 2 shows a photograph of lateral buds inoculated on gelled MS basal medium supplemented with auxin NAA, sucrose and myo-inositol.
Figure 3:
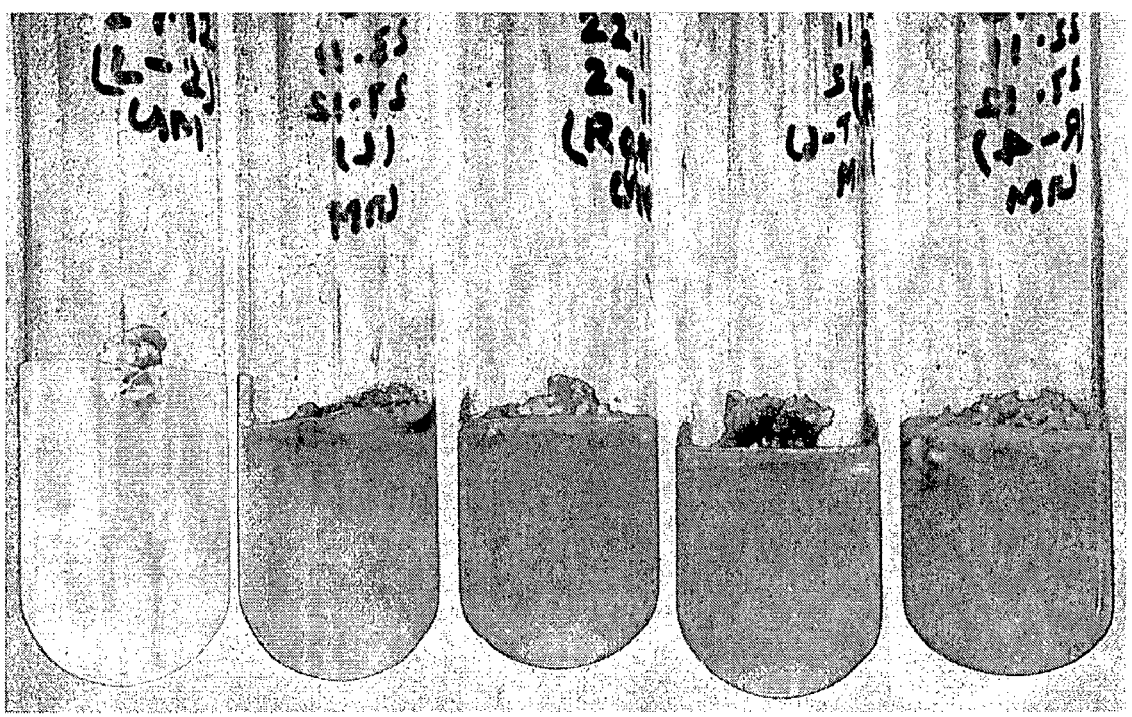
FIG. 3 shows a photograph of induction of rhizogenesis from lateral bud explants.
Figure 4:
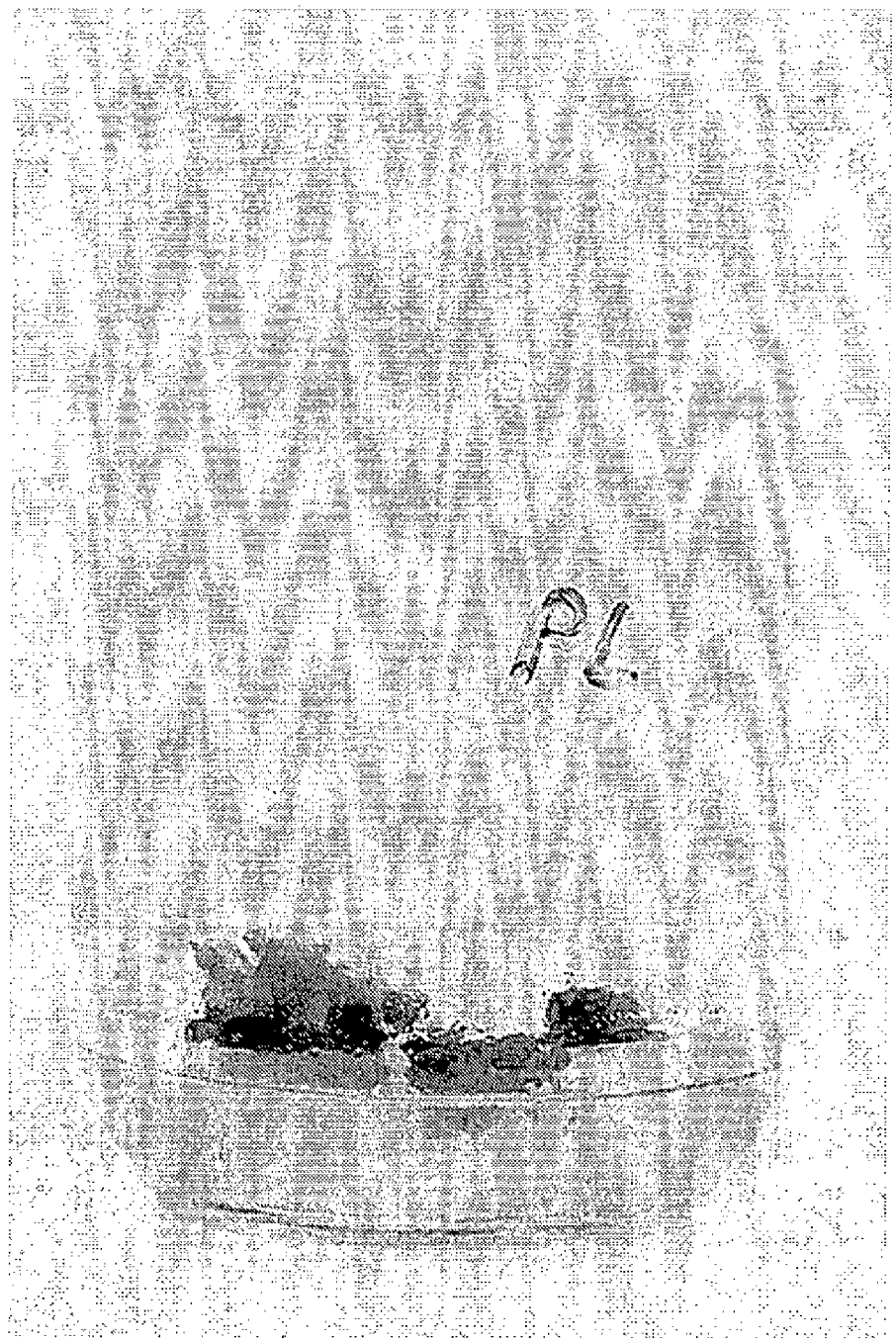
FIG. 4 shows a photograph of proliferation of shoot buds on MS basal medium supplemented with cytokinin BAP and sucrose and myo-inositol.
Figure 5:
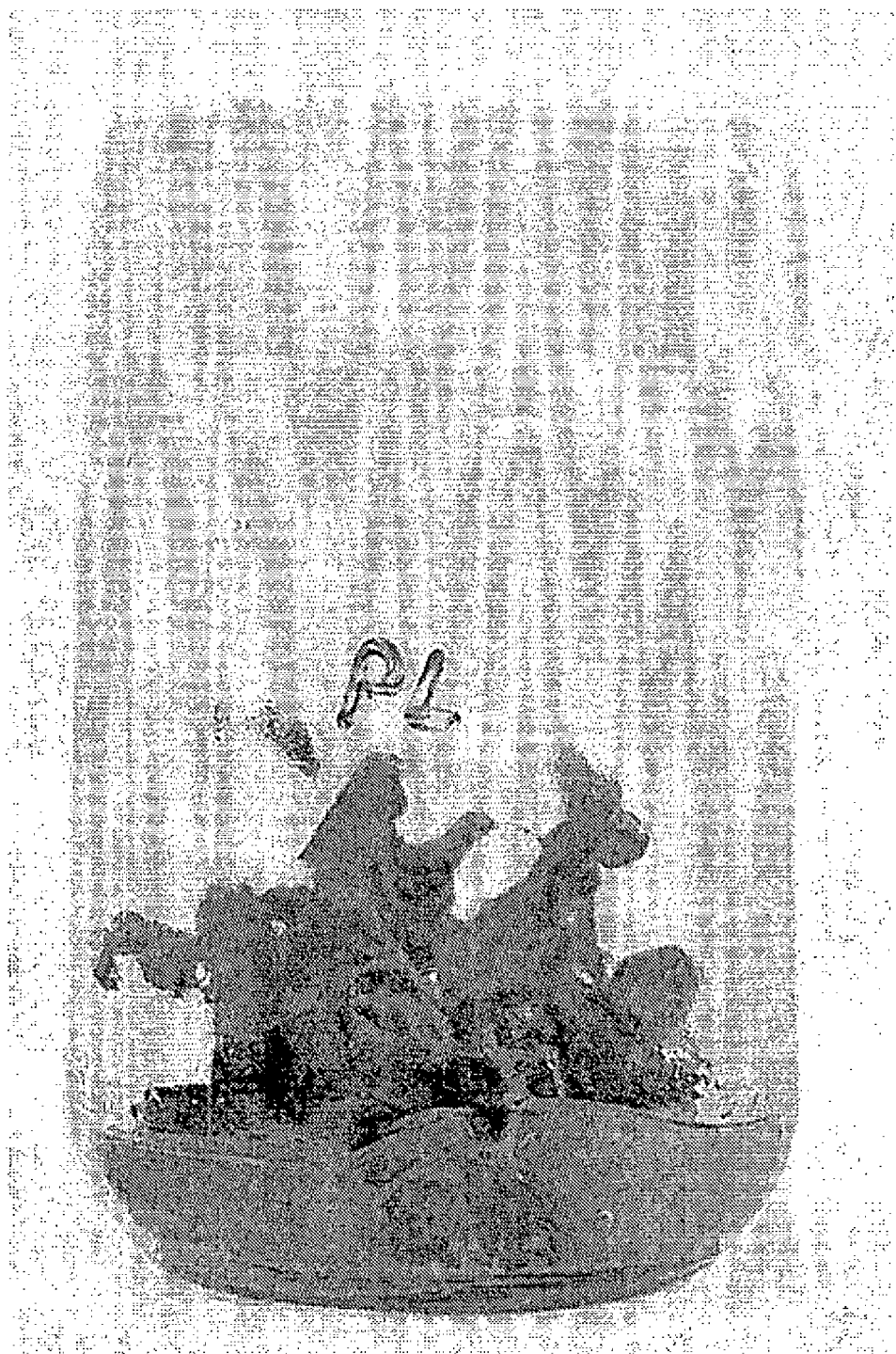
FIG. 5 shows a photograph of elongated shoots of *Piper longum*.
Figure 6:
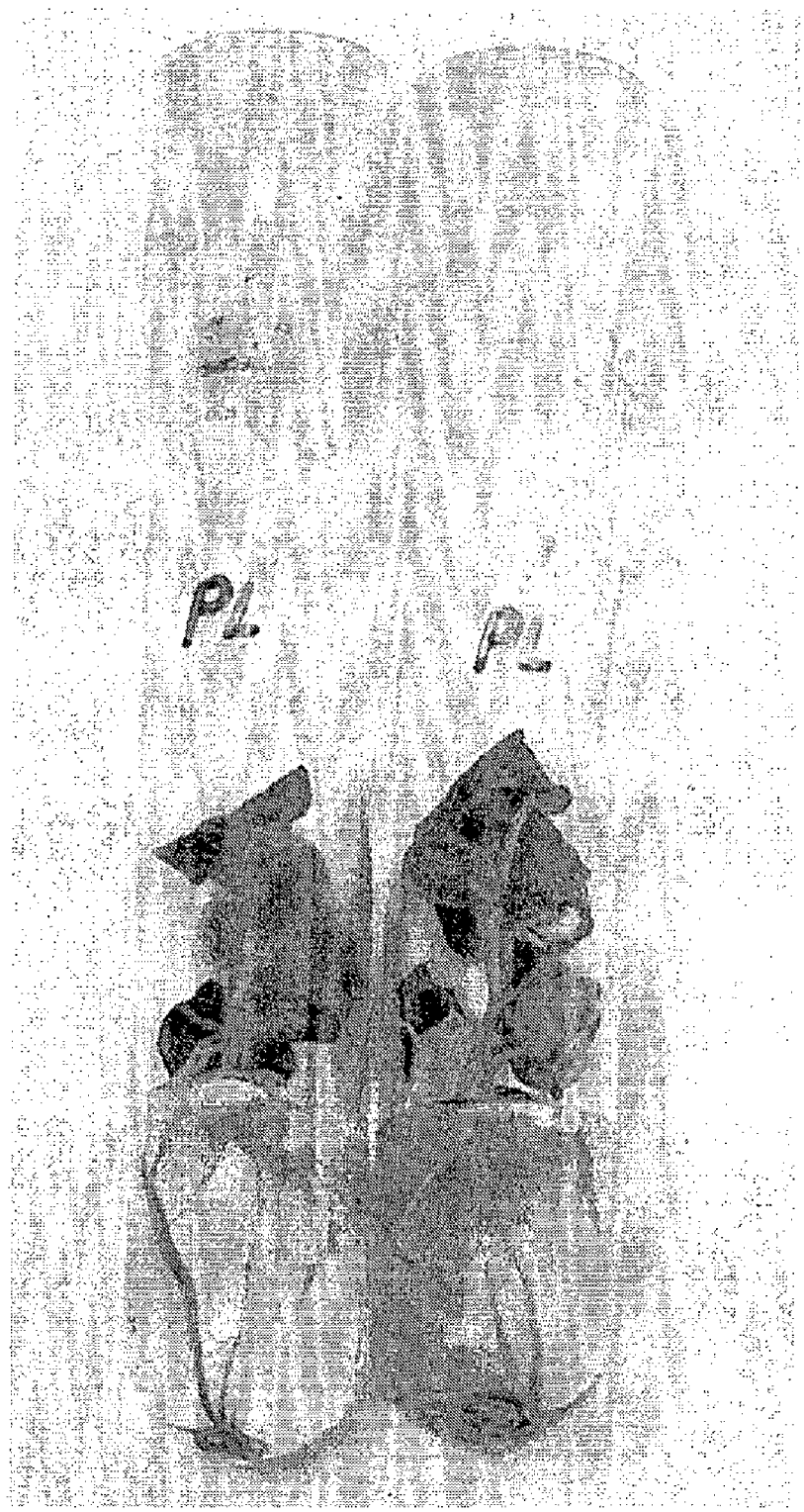
FIG. 6 shows a photograph of development of healthy roots from regenerated shoots.
Figure 7:
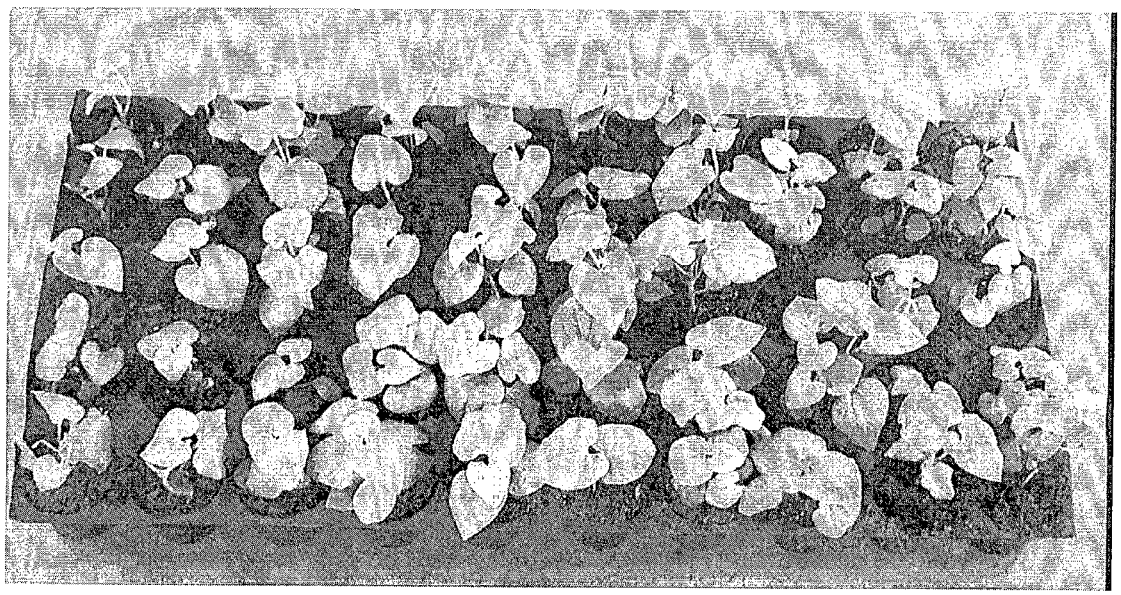
FIG. 7 shows a photograph of micropropagated plants which are being hardened in a portray in the green house having fan and pad system for cooling and foggers for maintaining relative humidity.

Specific description of applications of both somatic organonogenesis procedure and the further development of mature plants from somatic organonogenesis, are presented in the non limiting examples.

DETAILED DESCRIPTION OF THE INVENTION

Accordingly, the present invention provides an efficient method for micropropagation of *Piper longum* plant using lateral bud (meristematic) explant, said method comprising of the steps of:

A. Explant Collection and Surface Sterilization

Growing mother plant under controlled conditions in a green house or shade house to ensure a healthy mother plant, a source of explants.

Plants were regularly irrigated and given monthly foliar spray of a fungicide Bavistin (0.05-1%) and an insecticide Rogor (0.005-0.5%).

Giving an extra foliar spray of Bavistin (0.05-1%), two days prior to collecting the explants.

Collecting the explants from a mother plant by cutting a twig with a sharp scalpel, before 8 a.m. in the morning at a time when it has the highest turgor pressure, and immediately dipping the cut end into fungicide, Bavistin (0.05-1%) and bacteriacide, Ciprofloxacin solution (0.005-0.5%).

Washing the stem segment, after carefully removing the leaves with a sharp scalpel, using a mild detergent and running tap water.

Finally, rinsing the explants with demineralized water and dipping them in autoclaved distilled water and transferring them under Laminar Flow benches (LF) for final surface sterilization.

Dissecting lateral buds from the stem segments under LF and treating them with hydrogen chloride (HCl2) (0.002-0.2%) for 3 minutes and then giving three thorough rinses with autoclaved distilled water.

Further, surface sterilizing them by dipping in sodium hypochloride (NaOCl) (0.5-3%) for 4 minutes and again giving three thorough rinses with autoclaved distilled water.

B. Inoculation on Culture Initiation Medium

Preparing culture initiation medium by using MS basal medium described by Murashige and Skoog in 1968. To the MS basal medium, sucrose (2-4%), agar powder (0.7-1.2%), 100 mg/L myo-inositol and Naphthalene Acetic Acid (NAA) (0.01-0.5 mg/L) was added. This medium was autoclaved at 15 psi for 20 min and then cooled to solidify at room temperature.

Using sterilized forceps, each isolated and surface sterilized lateral bud was inoculated in a test tube containing 15 ml of above-mentioned medium; by placing the cut end of the lateral buds touching the medium.

Forceps were flamed using absolute alcohol just before each inoculation.

C. Incubation

Incubating the inoculated explants in dark at 23° C. +/−1° C. for 7-15 days. By this time, 6-7 root primordia appear from the basal cut end of all the lateral buds.

D. Induction of Organogenesis (Rhizogenesis)

Transferring incubated cultures in light having 2000-4000 lux light intensity.

A photoperiod of 16 hours was provided followed by a dark period of 8 hours daily.

Allowing each root to grow to an average size of 3 cm in 45 days.

E. Shoot Bud Proliferation & Shoot Elongation

Cutting each root into 1 cm long segments aseptically under LF.

Sub-culturing the 18 root segments separately onto MS basal medium supplemented with Benzyl Amino Purine (BAP) (0.5-3 mg/L), 2-4% sucrose, 100 mg/l myo-inositol and 0.7-1.2% agar for solidifying the medium.

Cultures were kept at 23° C. +/−1° C. under 2000-4000 Lux light intensity for a photoperiod of 16 hours followed by a dark period of 8 hours.

Each segment produced 50-55 adventitious shoot buds i.e. (18×50=900 shoot buds).

After 45 days each culture was cut into 2 pieces and each piece was sub-cultured in a separate culture bottle containing 25 ml of the same medium and growing them under similar physical conditions as mentioned above for shoot elongation for 45 days.

F. Rooting of Regenerated Shoots 2.5-3 cm long shoots with 2-3 nodes were carefully separated from the culture clumps using a sterile scalpel under LF.

Sub-culturing 10 separated shoots in a wide mouthed bottle containing MS basal medium fortified with Indole Butyric Acid (IBA) (1-3 mg/L), 2-4% sucrose, 100 mg/L myo-inositol and 0.7-1.2% agar.

Rooting of the regenerated shoots under reduced light 1000-3000 Lux for 28 days. Photoperiod and temperatures remains the same as before.

G. Hardening of Regenerated Plantlets

Removing the micropropagated plants carefully from the agar.

Washing the roots under tap water to remove any trace of agar adhered to the roots.

Dipping roots in Bavistin (0.05-1%) for half an hour.

Planting the micropropagated plantlets in 1:1 ratio of soil and cocopeat.

Growing them in green house having 80% relative humidity (RH) and a temperature below 28° C. for a first week and then gradually increasing the temperature to an ambient temperature of 30° C. to 32° C. and reducing the RH to 40% over a period of 4 weeks.

Transferring hardened plants (for acclimatization to plantation site conditions) to partial shade under shade-net for a week prior to transfer to the field.

EXAMPLE

A lateral bud (meristematic) explant from any position of a young or mature plant of *Piper longum* was taken and cultured in an MS basal medium supplemented with sucrose (2-4%), NAA (0.1-0.5 mg/l) and gelled with agar (0.7-1.2%). These were incubated in dark for 10 days at 23° C.±1° C. and transferred to a light intensity of 1000-3000 lux for 16 Hrs. followed by 8 Hrs. dark period resulting into rhizogenesis, producing 6-7 root like organs, by direct organogenosis from meristematic tissues of lateral buds, which grew up to 1.5 cm in length by 45th day of isolation.

The rhizogenic tissues were cut to 0.5 cm long segments with cytokinin BAP (0.5-3 mg/L) and solidified with agar (0.7-1.2%) resulting in adventitious shoot bud formation from all the root segments occurred on the same nutrient medium under similar physical conditions (2000-4000) lux light for 16 Hrs. followed by 8 Hrs. dark at 23° C. +/−1° C., the shoot buds elongated.

All separated shoots were responsive to IBA (0.1-3.1 mg/L) and produced healthy root system from the basal cut ends of these shoot in 4 weeks time.

Plantlets thus re-generated on transplant to in vivo on 1:1 soil & cocopeat in portrays having cavities showed good hardening. Hardened plants were transferred to shad net for secondary hardening (acclimatization) to ambient field conditions for 1-2 weeks and the plantlets were transferred to field for cultivation in conventional manner.

The abbreviations used in the text have the following meaning:

| | | |
|---|---|---|
| As defined herein NAA | is | Naphthalene Acetic Acid |
| As defined herein IAA | is | Indole Actetic Acid |
| As defined herein IBA | is | Indole Butyric Acid |
| As defined herein NOA | is | Naphthoxy Acetic Acid |
| As defined herein BAP | is | Benzylaminopurine |
| As defined herein Kinetin | is | 6-furfuryl amino purine |
| As defined herein 2-iP | is | 2-iso-Pentenyl adenine |
| As defined herein 2,4-D | is | 2,4-Dichlorobenzoic acid |
| As defined herein MS | is | Murashige & Skoog's medium (1962) |
| As defined herein B5 | is | Gramborg, O. L. et al's medium (1968) |
| As defined herein RH | is | Relative Humidity |

It is evident that these additional embodiments and variations which are not illustrated but are within the scope and spirit of the present invention. The above description and drawings are therefore intended to be exemplary only and the scope of the invention is to be limited by the appended claims.

We claim:

1. A method of in-vitro micropropagation of *Piper longum* by direct rhizogenesis from a lateral bud explant, said method comprising the steps of:
   i. cutting the lateral buds from stem segments under laminar flow benches (LF) and treating them with hydrogen chloride (HCl2) (0.002-0.2%) for 3 minutes and rinsing the treated lateral buds with autoclaved distilled water;
   ii. subjecting the lateral buds to a surface sterilization by dipping into sodium hypochloride (NaOCl) (0.5-3%) for 4 minutes and again treating the dipped lateral buds with three additional thorough rinses with autoclave distilled water;
   iii. inoculating the surface sterilized lateral buds in a culture initiation medium supplemented with auxin;
   iv. incubating the inoculated explants in dark at 23° C.±1° C., for 7-15 days to produce 6-7 root primordia from basal cut ends of all the lateral buds;
   v. transferring the incubated cultures of step iv, into a light intensity of 2000-4000 lux and providing a photoperiod of 16 hours followed by a dark period of 8 hours daily;
   vi. allowing each root to grow to an average size of 1.5 cm in 45 days; through direct rhizogenesis;
   vii. cuting each root of step vi, into 0.5 cm long segments aseptically under LF;
   viii. sub-culturing the 18 segments procured from a single explant separately onto a shoot induction medium supplemented with the auxin to produce cultures;
   ix. keeping the cultures of step viii, at 23° C. under a light intensity of 2000-4000-lux for a photoperiod of 16 hours followed by a dark period of 8 hours to produce 50-55 adventitious shoot buds and 900 shoot buds (18×50);
   x. cutting each culture clump into two pieces after a 45 day interval and sub-culturing each piece in a separate culture bottle containing 25 ml of the same medium, and growing them under similar physical conditions as mentioned in step ix, for a period of 45 days for shoot elongation;
   xi. separating 2.5-3 cm long shoots with 2-3 nodes from the culture clumps using a sterile scalpel under LF;
   xii. sub-culturing 10 separated shoots of step xi, in a wide mouth bottle containing rooting medium supplemented with the auxin;
   xiii. rooting the regenerated shoots of step xii, under a reduced light intensity of 1000-3000 lux for a period of 28 days, with a 16 hour photoperiod and temperature 23° C.±1° C.;
   xiv. removing the micropropagated plants carefully from the agar contained in the sub-culturing medium;
   xv. washing the roots of the micropropagated plants of step xiv, under tap water to remove any trace of agar adhered to the roots and dipping the roots in Bavistin (0.05-1%) for half an hour; and
   xvi. planting the micropropagated plantlets in 1:1 ratio of soil and cocopeat.

2. The method according to claim 1, wherein the culture initiation medium used is MS basal medium, sucrose (1-5%), agar powder (0.2-1%), 100 mg/L myo-inositol supplemented with the auxin.

3. The method according to claim 2, wherein the auxin is Naphthalene Acetic Acid (NAA) (0.01-0.5 mg/L).

4. The method according to claim 1, wherein the shoot induction medium comprises MS basal medium, sucrose (1-5%), agar powder (0.2-1%), myo-inositol (100 mg/L) supplemented with the cytokinin.

5. The method according to claim 4, wherein cytokinin is Benzyl Amino Purine (BAP) (0.5-3 mg/L).

6. The method according to claim 1, wherein the rooting medium comprises MS basal medium, sucrose (1-5%), agar powder (0.2-1%), myo-inositol (100 mg/L) supplemented with the auxin.

7. The method according to claim 6, wherein the auxin is Indole Butyric Acid (IBA) (1-3 mg/L).

* * * * *